United States Patent [19]

Moran, Jr. et al.

[11] Patent Number: 5,468,900
[45] Date of Patent: Nov. 21, 1995

[54] CONVERSION OF NYLON 6 AND/OR NYLON 6,6 TO ADIPIC ACID

[75] Inventors: Edward F. Moran, Jr., Gibbstown, N.J.; Ronald J. McKinney, Wilmington, Del.

[73] Assignee: E. I. Du Pont de Nemours and Company, Wilmington, Del.

[21] Appl. No.: 314,744

[22] Filed: Sep. 29, 1994

[51] Int. Cl.$^6$ .................................................. C07C 55/14
[52] U.S. Cl. ................................ 562/590; 562/590
[58] Field of Search ................................ 562/590, 593

[56] References Cited

U.S. PATENT DOCUMENTS 3,069,465  12/1962  Monet ................................ 260/537
3,806,543  4/1974  Takata et al. ........................ 260/526
5,310,905  5/1994  Moran, Jr. .......................... 540/540

FOREIGN PATENT DOCUMENTS 910056  3/1954  Germany.
56-3865  1/1981  Japan ............................ C07D 201/12

*Primary Examiner*—José G. Dees
*Assistant Examiner*—Rosalynd A. Williams

[57] ABSTRACT

Waste nylon 6 and/or nylon 6,6 are converted to adipic acid monomer by depolymerization with an aliphatic monocarboxylic acid to form alkylamides followed by oxidation of the alkylamides to adipic acid.

15 Claims, No Drawings

CONVERSION OF NYLON 6 AND/OR NYLON 6,6 TO ADIPIC ACID

BACKGROUND OF THE INVENTION

1. Field of the Invention

The present invention concerns a process for converting nylon 6, nylon 6,6 or mixtures thereof to a single monomer species, adipic acid. More specifically, the invention concerns a process comprising reacting nylon 6 and/or nylon 6,6 with an aliphatic monocarboxylic acid of the formula, $H_3C—(CH_2)_n—C(=O)—OH$, where n is 0 to 4 to form alkylamido monomer species, and oxidizing the alkylamido monomer species to adipic acid.

2. Description of Related Art

There is waste associated with the manufacture of any man-made article and the disposal thereof after it has served its useful life. For purposes of both economy and environmental considerations it is desirable to recover as much of the value of the material as possible. Although incineration may be employed to recover some value as fuel, recovery of the material from which an article was originally fashioned so that it may be reused is a worthwhile objective.

Nylon 6 and nylon 6,6 form the vast majority of polyamides found in commercial use worldwide. Distinguishing between these two polyamides requires sophisticated test methods. There is a great need for a method to process both polymers without separating them from each other to yield an intermediate material that can be reused to produce new nylon.

Numerous methods to depolymerize nylon are known. Nylon 6 is routinely depolymerized under the influence of steam to caprolactam for reuse by nylon 6 producers. Other methods have been reported, such as hydrolysis of nylon 6 to aminocaproic acid in aqueous barium hydroxide solutions as described in Kowolik et al., published British patent application GB 790,503. Processes for depolymerizing nylon 6,6 for reuse are also known. Monet, U.S. Pat. No. 3,069,465 describes a method for depolymerizing nylon 6,6 with aqueous sulfuric acid, recovering adipic acid and, after neutralization, hexamethylene diamine. Habermann et al., German published patent application DE 4,219,757 describes a method for the depolymerization of nylon 6,6 by aqueous base solution, separation of the diamine by extraction and converting the diacid salt into the corresponding diacid by electrolysis.

Recovery of useful monomers from mixtures of nylon 6 and 6,6 are less well known in the art. Moran, U.S. Pat. No. 5,266,694 discloses the recovery of caprolactam and hexamethylene diamine from a nylon 6/6,6 mixture under the influence of steam in the presence of a basic catalyst. McKinney, U.S. Pat. No. 5,302,756 describes the ammonolysis of mixed nylons to produce a mixture of monomers suitable for conversion to hexamethylene diamine.

Depolymerization of nylon 6,6 or mixtures thereof with nylon 6 generally produces multiple monomer products which must be separated from one another or subject to further modification prior to reuse. Another hindrance to efficient production of monomer species from waste nylon is the separation of the nylon fraction from composite materials, such as carpets. This is usually accomplished mechanically, adding to the expense.

There is high value in a process that can treat composite materials containing mixed nylons with a solution of a reagent that can both separate the nylons from the foreign material, depolymerize the nylons and convert the depolymerized nylon into a single monomer product suitable for reuse in producing new nylon.

SUMMARY OF THE INVENTION

The present invention provides a method for recovery of the caprolactam values from polycaprolactam as adipic acid comprising supplying an acid of the formula $$H_3C—(CH_2)_n—C(=O)—OH$$

where n is 0 to 4 and the polycaprolactam to an autoclave in the amount of at least one mole of acid for every mole of repeat units of the polymer, heating the mixture at a temperature of at least 150° C., at autogenous pressure or greater for a time sufficient to depolymerize the polymer and form 6-alkylamidohexanoic acid, oxidizing the 6-alkylamidohexanoic acid to a mixture of adipic acid and alkylamide, and separating the adipic acid from the mixture.

Also provided is a method for converting polyhexamethylene adipamide to adipic acid comprising supplying an acid of the formula $$H_3C—(CH_2)_n—C(=O)—OH$$

where n is 0 to 4 and the polyhexamethylene adipamide to an autoclave in the amount of at least two moles of acid for every mole of repeat units of the polymer, heating the mixture at a temperature of at least 150° C., at autogenous pressure or greater for a time sufficient to depolymerize the polymer and form a mixture of adipic acid and N,N'-hexamethylene bisalkylamide, oxidizing the N,N'-hexamethylene bisalkylamide to a mixture of adipic acid and alkylamide and separating the adipic acid from the mixture.

A further provision is a process for converting a mixture of polycaprolactam and polyhexamethylene adipamide to adipic acid comprising supplying an acid of the formula $$H_3C—(CH_2)_n—C(=O)—OH$$

where n is 0 to 4 and the mixture of the polymers to an autoclave in the amount of at least one mole of acid for every mole of repeat units of polycaprolactam and at least two moles of acid for every mole of repeat units of polyhexamethylene adipamide, heating the mixture at a temperature of at least 150° C., at autogenous pressure or greater for a time sufficient to depolymerize both polymers and form a mixture of 6-alkylamidohexanoic acid, adipic acid and N,N'-hexamethylene bisalkylamide, oxidizing the 6-alkylamidohexanoic acid and N,N'-hexamethylene bisalkylamide to a mixture of adipic acid and alkylamide and separating the adipic acid from the mixture.

DETAILED DESCRIPTION OF THE INVENTION

The method of the current invention can be used to process either nylon 6 or nylon 6,6 alone or mixtures thereof. It accommodates the variability of feed which would be expected when mixed consumer and industrial nylon waste is processed. As a further advantage, mixtures of nylon 6 and nylon 6,6 are converted to a single monomer product, adipic acid.

The depolymerization of nylon 6 and/or nylon 6,6 using aliphatic monocarboxylic acids is described in Moran, U.S. Pat. No. 5,310,905, the disclosure of which is hereby incorporated by reference.

As applied to nylon 6, the process of the current invention involves treating the nylon 6 (polycaprolactam) in an autoclave with an aliphatic monocarboxylic acid of the formula $$H_3C-(CH_2)_n-C(=O)-OH$$

where n is an integer of from 0 to 4, and heating the mixture at a temperature of at least 150° C. to form 6-alkylamidohexanoic acid. While a temperature of 150° C. is useful, preferred temperatures are in excess of about 200° C. and preferably above about 250° C. Ordinarily, the process proceeds at autogenous pressure, however while no benefit is known to result from it, greater pressure may be employed if desired. The alkyl group corresponds to the alkyl chain of the carboxylic acid that was used to treat the nylon polymer. Suitable aliphatic acids include acetic acid and propionic acid. The acid should be present in an amount of at least one mole of acid for every mole of repeat unit of the polymer. The acid and polycaprolactam may be charged to the autoclave separately or as a solution of the polymer in the acid as would be obtained if the acid were used as a solvent to separate the nylon from other material it may be associated with in a composite product such as a carpet. An excess of acid is generally employed to provide a solvent medium and to hasten the complete depolymerization of the nylon 6.

The oxidation of the depolymerization product, 6-alkylamidohexanoic acid, to yield adipic acid, can be carried out by a variety of oxidation techniques. For example, an oxidation catalyst and source of oxygen can be supplied to the autoclave and the oxidation carried out simultaneously with the depolymerization. Suitable oxygen sources include air, oxygen gas or hydrogen peroxide. Alternatively the oxidation can be carried out in a like manner in a subsequent step after the depolymerization is complete.

The oxidation may also be carried out electro-chemically. The depolymerization products may be isolated from the depolymerization reaction mixture and redissolved in a suitable solvent containing an electrolyte prior to electrolysis. Alternatively, an electrolyte may be added directly to the polymerization reaction mixture, avoiding the need for isolating the depolymerization products. Optionally, an oxidation catalyst may be added to the solution. The mixture being oxidized may be checked periodically and the process continued until substantial amounts of adipic acid have been produced. Alternatively, the oxidation may be continued until the theoretical number of coulombs have been passed. At that point the solvent can be removed and the adipic acid recovered from the mixture containing the other reaction product, alkylamide, by crystallization or by other means.

The process as applied to nylon 6,6 is similar to that for nylon 6 with two exceptions. The first is that at least two moles of aliphatic carboxylic acid are required for every mole of repeat units of the nylon polymer. The second distinction is that the depolymerization product is a mixture of adipic acid and N,N'-hexamethylene bisalkylamide. The alkyl group corresponds to the alkyl chain of the carboxylic acid that was used to treat the nylon polymer.

The oxidation of the depolymerized nylon 6,6 can be carried out using the methods described above for oxidizing the reaction products of carboxylic acid depolymerized nylon 6. The presence of adipic acid resulting from the depolymerization of nylon 6,6 has no effect on the oxidation step since the products resulting from oxidation of the N,N'-hexamethylene bisalkylamide are adipic acid and alkylamide. Incomplete oxidation of N,N'-hexamethylene bisalkylamide results in formation of 6-alkylamidohexanoic acid, the depolymerization product of nylon 6. Further oxidation converts the 6-alkylamidohexanoic acid to adipic acid.

The process of the current invention is especially advantageous for processing mixtures of both nylon 6 and nylon 6,6 polymers. The ability to process both in a single process without prior separation to yield a single product is of great benefit. The process proceeds in a similar manner to each of the recovery processes for nylon 6 and nylon 6,6 respectively, as described above. The aliphatic acid should be added in an amount of at least one mole for every mole of repeat units of the polycaprolactam present in the polymer mixture and at least two moles of the acid should be added for every mole of repeat units of the polyhexamethylene adipamide present in the polymer mixture. The resulting product contains adipic acid in admixture with 6-alkylamidohexanoic and N,N'-hexamethylene bisalkylamide which are subsequently oxidized to adipic acid and alkylamide as described above.

If composite materials such as carpeting are being processed, the nylons may be dissolved in the aliphatic carboxylic acid by heating and the insolubles removed by filtration. For example, in the processing of waste nylon carpet, the waste carpet may be heated to temperatures between about 100° to 110° C. at atmospheric pressure in the aliphatic monocarboxylic acid solvent. Upon dissolution of the nylon face fibers, the solution can be filtered while hot to remove any insoluble materials such as primary and secondary backing components and binder materials, including latex rubbers and fillers. The filtrate is then processed according to the invention to depolymerize the dissolved nylon.

The invention is described further in the examples which follow, but these examples should not be construed to limit the scope of the invention. Parts and percentages are by weight unless otherwise noted.

EXAMPLES

EXAMPLE 1

This example illustrates the oxidation of 6-acetamidohexanoic acid, the primary acetylation product of nylon 6, in the presence of an oxidation catalyst. The 6-acetamidohexanoic acid was obtained from Aldrich Chemical Company, Milwaukee, Wis.

A flask was charged with: 14.4 grams (83.4 mmoles) 6-acetamidohexanoic acid, 1.24 grams of an oxidation catalyst composed of cobalt(ous) acetate, manganese acetate tetrahydrate, and 48% HBr solution, and 150 grams acetic acid.

The mixture was stirred until everything dissolved. The flask was heated with an electric heating mantle and a slow flow of air introduced via a gas dispersion tube. The mixture was heated at temperatures between 93° and 104° C. for 24 hours while maintaining the air flow. At the end of heating period a sample examined by GC/MS revealed the major components to be unreacted 6-acetamidohexanoic acid, acetamide and adipic acid. The total reaction mixture was analyzed by calibrated liquid chromatography and found to contain 1.39 g adipic acid and 6.76 g 6-acetamidohexanoic acid. This represents 53% conversion of 6-acetamidohexanoic acid to yield 21.5% adipic acid on a molar basis.

EXAMPLE A (COMPARATIVE)

This example demonstrates that no oxidation occurs when 6-acetamidohexanoic acid is heated in the absence of an oxidation catalyst.

A flask set-up similar to that of Example 1 was charged with 14.4 grams (83.4 mmoles) 6-acetamidohexanoic acid and 150 grams acetic acid and stirred until everything was in solution. The flask was heated with an electric heating mantle and a slow flow of air introduced via the gas dispersion tube. The mixture was heated at temperatures between 105° and 108° C. for 24 hours while maintaining the air flow. At the end of the heating period a sample examined by GC only detected unreacted 6-acetamidohexanoic acid and caprolactam, no adipic acid or acetamide were detected. The total reaction mixture was analyzed by calibrated liquid chromatography and found to contain a nearly quantitative recovery of 6-acetamidohexanoic acid plus caprolactam equivalent to the 14.4 grams of 6-acetamidohexanoic acid charged.

EXAMPLE 2

This example illustrates the simultaneous depolymerization and oxidation of polycaprolactam.

A set-up similar to that of Example 1 was charged with a solution of:

4.96 grams of an oxidation catalyst composed of cobalt(ous) acetate, manganese acetate tetrahydrate and 48% HBr solution, and 600 grams acetic acid.

37.6 grams of sheared nylon 6 carpet fiber was added to this solution. The flask contents were heated to 115° C. at which point all the nylon had dissolved and the air sparge was started. The mixture was heated at temperatures between 105° and 115° C. for 10 days while maintaining the air flow. At the end of the heating period the total reaction mixture was diluted to 1000 mL with water for analysis. Solid precipitation occurred indicating incomplete depolymerization of the nylon. The liquid fraction was analyzed by calibrated liquid chromatography and found to contain 0.16 g adipic acid and 0.45 g 6-acetamidohexanoic acid. This represents 0.33% adipic acid and 0.78% 6-acetamidohexanoic acid yield on a molar basis from the original nylon 6 carpet fiber.

EXAMPLE 3

This example illustrates the oxidation of N,N'-hexamethylene bisacetamide, an acetylation product of nylon 6,6 in acetic acid. The N,N'-hexamethylene bisacetamide was obtained from Aldrich Chemical Company, Milwaukee, Wis.

A flask was charged with 14.6 grams (73 mmoles) N,N'-hexamethylene bisacetamide, 1.0 grams cobalt(ous) acetate, 50 grams 50% hydrogen peroxide solution, and 100 grams acetic acid and stirred, whereupon the flask contents heated up to 104° C. due to the heat of reaction. After refluxing at 104° C. for approximately 3 minutes the reaction mixture gradually cooled. It was then heated at 54°–60° C. with a slow flow of air via the gas dispersion tube for 24 hours. At the end of heating period a sample examined by GC revealed unreacted N,N'-hexamethylene bisacetamide and acetamide. The total reaction mixture was analyzed by calibrated liquid chromatography and found to contain 1.49 g adipic acid, 1.46 g 6-acetamidohexanoic acid and 5.91 g N,N'-hexamethylene bisacetamide. This represents 59.5% conversion of N,N'-hexamethylene bisacetamide to yield 23.5% adipic acid and 19.4% 6-acetamidohexanoic acid on a molar basis.

EXAMPLE 4

This example illustrates the simultaneous depolymerization and oxidation of polyhexamethylene adipamide.

A flask was charged with a solution of 4.0 grams cobalt(ous) acetate, 24.0 grams sodium acetate, 400 grams of acetic acid, and 200 grams acetic anhydride. To this was added 66 grams of sheared nylon 6,6 carpet fiber. The flask contents were heated to 125° C. Although all the nylon had not dissolved at that point an air sparge was started. The mixture was heated at temperatures between 99° and 125° C. for 10 days while maintaining the air flow. After 2 days the nylon was completely dissolved. The total reaction mixture was analyzed by calibrated liquid chromatography and found to contain 30.8 g adipic acid, 14.8 g N,N'-hexamethylene bisacetamide. and 1.80 g 6-acetamidohexanoic acid. This represents 36.2% adipic acid, 25.4% N,N'-hexamethylene bisacetamide, and 3.6% 6-acetamidohexanoic acid yield from the original nylon 6,6 carpet fiber on a molar basis.

EXAMPLE 5

This example illustrates the electrochemical oxidation of 6-acetamidohexanoic acid, the primary acetylation product of nylon 6. The 6-acetamidohexanoic acid was obtained from Aldrich Chemical Company, Milwaukee, Wis.

A single compartment electrolytic cell fitted with 1 inch square parallel platinum foil electrodes, one inch apart was charged with 7.2 grams (41.7 mmoles) 6-acetamidohexanoic acid, 0.09 g Cobalt(ous) acetate and 75 ml 0.75 molar sulfuric acid solution. The contents of the cell were stirred with a magnetic stirrer bar during the electrolysis. The electrodes were connected to an electrical circuit containing a suitable direct current power supply, an ammeter and a coulometer. The electrolysis was conducted at a current of 480 milliamperes at a cell voltage of 2.9 volts for a sufficient time to accumulate 8074 coulombs. At the end of the run a sample examined by GC/MS revealed the major components to be 6-acetamidohexanoic acid, adipic acid and 5-formyl valeric acid. The product mixture was found to contain 2.18 grams of adipic acid and 3.56 grams of 6-acetamidohexanoic acid by quantitative analysis by calibrated liquid chromatography. This indicates a 50.6% conversion of 6-acetamidohexanoic acid, 70.7% yield to adipic acid on a molar basis at 71.3% current efficiency.

EXAMPLE 6

This example illustrates the electrochemical oxidation of N,N'-hexamethylene bisacetamide, an acetylation product of nylon 6,6. The N,N'-hexamethylene bisacetamide was obtained from Aldrich Chemical Company, Milwaukee, Wis.

The same electrolysis apparatus as in Example 5 was used. The cell was charged with 4.17 grams (20.85 mmoles) N,N'-hexamethylene bisacetamide, 0.09 g Cobalt(ous) acetate and 75 ml 0.75 molar sulfuric acid solution. The electrolysis was conducted at a current of 480 millamperes at a cell voltage of 3.1 volts for a sufficient time to accumulate 8050 coulombs At the end of the run a sample examined by GC/MS revealed the major components to be N,N'-hexamethylene bisacetamide, 6-acetamidohexanoic acid, adipic acid, 5-formyl valeric acid and 6-acetamidocaproaldehyde. The product mixture was found to contain 0.34 grams of adipic acid, 0.28 grams of 6-acetamidohexanoic acid and 1.65 grams N,N'-hexamethylene bisacetamide by quantitative analysis by calibrated liquid chromatography. This indicates a 60.4% conversion of N,N'-hexamethylene bisacetamide, 13.1% yield to 6-acetamidohexanoic acid and 18.2% yield to adipic acid on a molar basis.

EXAMPLE 7

This example illustrates electrochemical oxidation of N,N'-hexamethylene bisacetamide, an acetylation product of nylon 6,6, in acetic acid solvent with added electrolyte. The N,N'-hexamethylene bisacetamide was obtained from Aldrich Chemical Company, Milwaukee, Wis.

The same electrolysis apparatus as in Example 5 was used. The cell was charged with 4.17 grams (20.85 mmoles) N,N'-hexamethylene bisacetamide, 0.09 g Cobalt(ous) acetate and 75 ml 0.75 molar sulfuric acid solution in 90% aqueous acetic acid. A steady flow of air was passed through the solution via a gas dispersion tube. The electrolysis was conducted at a current of 480 millamperes at a cell voltage of 9.5 volts for a sufficient time to accumulate 16,100 coulombs. The product mixture was found to contain 0.67 grams of adipic acid, 0.36 grams of 6-acetamidohexanoic acid and 1.81 grams N,N'-hexamethylene bisacetamide by quantitative analysis by calibrated liquid chromatography. This indicates a 56.6% conversion of N,N'-hexamethylene bisacetamide, 17.9% yield to 6-acetamidohexanoic acid and 39.0% yield to adipic acid on a molar basis.

We claim:

1. A method for converting polycaprolactam to adipic acid comprising supplying an acid of the formula $$H_3C-(CH_2)_n-C(=O)-OH$$

where n is 0 to 4 and the polycaprolactam to an autoclave in the amount of at least one mole of acid for every mole of repeat units of the polymer, heating the mixture at a temperature of at least 150° C., and at autogenous pressure or greater for a time sufficient to depolymerize the polymer and form 6-alkylamidohexanoic acid, oxidizing the 6-alkylamidohexanoic acid to a mixture of adipic acid and alkylamide, and separating the adipic acid from the mixture.

2. The method of claim 1, wherein the polycaprolactam is from waste material.

3. The method of claim 2, wherein the waste material is the pile fiber of carpets.

4. The method of claim 1, wherein the 6-alkylamidohexanoic acid is oxidized in the presence of an oxidation catalyst.

5. The method of claim 1, wherein the 6-alkylamidohexanoic acid is oxidized electrochemically.

6. A method for converting polyhexamethylene adipamide to adipic acid comprising supplying an acid of the formula $$H_3C-(CH_2)_n-C(=O)-OH$$

where n is 0 to 4 and the polyhexamethylene adipamide to an autoclave in the amount of at least two moles of acid for every mole of repeat units of the polymer, heating the mixture at a temperature of at least 150° C., and at autogenous pressure or greater for a time sufficient to depolymerize the polymer and form a mixture of adipic acid and N,N'-hexamethylene bisalkylamide, oxidizing the N,N'-hexamethylene bisalkylamide to a mixture of adipic acid and alkylamide and separating the adipic acid from the mixture.

7. The method of claim 6, wherein the polyhexamethylene adipamide is from waste material.

8. The method of claim 7, wherein the waste material is the pile fiber of carpets.

9. The method of claim 5, wherein the N,N'-hexamethylene bisalkylamide is oxidized in the presence of an oxidation catalyst.

10. The method of claim 6, wherein the N,N'-hexamethylene bisalkylamide is oxidized electrochemically.

11. A method for converting a mixture of polycaprolactam and polyhexamethylene adipamide to adipic acid comprising supplying an acid of the formula $$H_3C-(CH_2)_n-C(=O)-OH$$

where n is 0 to 4 and the mixture of the polymers to an autoclave in the amount of at least one mole of acid for every mole of repeat units of polycaprolactam and at least two moles of acid for every mole of repeat units of polyhexamethylene adipamide, heating the mixture at a temperature of at least 150° C., and at autogenous pressure or greater for a time sufficient to depolymerize both polymers and form a mixture of 6-alkylamidohexanoic acid, adipic acid and N,N'-hexamethylene bisalkylamide, oxidizing the 6-alkylamidohexanoic acid and N,N'-hexamethylene bisalkylamide to a mixture of adipic acid and alkylamide and separating the adipic acid from the mixture.

12. The method of claim 11, wherein the mixture of polymers is from waste material.

13. The method of claim 12, wherein the waste material is the pile fiber of carpets.

14. The method of claim 11, wherein the 6-alkylamidohexanoic acid and N,N'-hexamethylene bisalkylamide are oxidized in the presence of an oxidation catalyst.

15. The method of claim 11, wherein the 6-alkylamidohexanoic acid and N,N'-hexamethylene bisalkylamide are oxidized electrochemically.

* * * * *